United States Patent
Freedland

(10) Patent No.: US 7,097,654 B1
(45) Date of Patent: Aug. 29, 2006

(54) FLIP-WING TISSUE RETAINER

(76) Inventor: Yosef Freedland, 64/6 Trumpeldor Street, Petach-Tikva 49403 (IL)

( * ) Notice: Subject to any disclaimer, the term of this patent is extended or adjusted under 35 U.S.C. 154(b) by 387 days.

(21) Appl. No.: 10/169,062

(22) PCT Filed: Oct. 7, 2000

(86) PCT No.: PCT/US00/27526

§ 371 (c)(1),
(2), (4) Date: Jul. 2, 2002

(87) PCT Pub. No.: WO01/49190

PCT Pub. Date: Jul. 12, 2001

Related U.S. Application Data

(60) Provisional application No. 60/174,386, filed on Jan. 3, 2000, provisional application No. 60/193,000, filed on Mar. 28, 2000.

(30) Foreign Application Priority Data

Mar. 28, 2000 (WO) .............................. IB00/00364

(51) Int. Cl.
*A61B 17/04* (2006.01)
*A61F 2/30* (2006.01)
*A61F 2/08* (2006.01)

(52) U.S. Cl. ............ 606/232; 606/72; 623/13.13

(58) Field of Classification Search ........... 606/72, 606/74, 151, 232; 623/13.11–13.2; 411/340, 411/345

See application file for complete search history.

(56) References Cited

U.S. PATENT DOCUMENTS

| | | |
|---|---|---|
| 436,101 A | 9/1890 | Orr |
| 590,294 A | 9/1897 | Archer |
| 624,969 A | 5/1899 | Peterson |
| 726,636 A | 4/1903 | Carll |
| 826,131 A | 7/1906 | Weaver |
| 1,963,514 A | 6/1934 | Wherren |
| 2,017,114 A | 10/1935 | Winchester |
| 2,077,804 A | 4/1937 | Morrison |
| 2,485,531 A | 10/1949 | Dzus et al. |
| 2,489,870 A | 11/1949 | Dzus |
| 2,625,357 A | 1/1953 | Atkinson |
| 3,332,118 A | 7/1967 | Temple et al. |
| 3,903,549 A | 9/1975 | Deyerle |
| 4,262,369 A | 4/1981 | Roux |
| 4,589,179 A | 5/1986 | Hulting, Jr. |
| 4,721,103 A | 1/1988 | Freedland |
| 4,862,883 A | 9/1989 | Freeland |
| 4,903,692 A | 2/1990 | Reese |

(Continued)

FOREIGN PATENT DOCUMENTS

FR        2 750 031        12/1997

(Continued)

*Primary Examiner*—Julian W. Woo

(57) ABSTRACT

An orthopedic flip-wing tissue retainer (2) comprises a flip-wing (7), tissue-retaining means (8) and a joint formed between the flip-wing (7) and the tissue-retaining means (8). The tissue retainer (2) is easily installed and used to anchor a biological tissue. The tissue retainer (2) can be used in combination with other devices to replace or repair a ligament or tendon in a joint. In particular, when used for ligament replacement, the tissue retainer (2) eliminates or at least minimizes the twisting that typically occurs during conventional surgery. In addition, the tension of the ligament graft can be precisely adjusted by using a tension-adjusting device (3 or 203) in combination with the flip-wing tissue retainer (2). The tension-adjusting device (203) can include a ball (204)-and-socket (205) joint.

4 Claims, 9 Drawing Sheets

U.S. PATENT DOCUMENTS

| | | | |
|---|---|---|---|
| 5,002,574 A * | 3/1991 | May et al. ............... | 623/13.13 |
| 5,098,433 A | 3/1992 | Freedland | |
| 5,108,433 A | 4/1992 | May et al. | |
| 5,383,905 A | 1/1995 | Golds et al. | |
| 5,429,641 A | 7/1995 | Gotfried | |
| 5,562,668 A * | 10/1996 | Johnson ....................... | 606/72 |
| 5,601,562 A | 2/1997 | Wolf et al. | |
| 5,626,590 A | 5/1997 | Wilk | |
| 5,643,266 A | 7/1997 | Li | |
| 5,755,808 A | 5/1998 | DeCarlo et al. | |
| 5,916,216 A | 6/1999 | DeSatnick et al. | |
| 5,919,194 A | 7/1999 | Anderson | |
| 5,951,605 A | 9/1999 | Dennis et al. | |
| 5,997,541 A | 12/1999 | Schenk | |
| 6,045,361 A | 4/2000 | Misch et al. | |
| 6,068,648 A | 5/2000 | Cole et al. | |
| 6,086,591 A | 7/2000 | Bojarski | |
| 6,099,568 A | 8/2000 | Simonian et al. | |
| 6,440,134 B1 * | 8/2002 | Zaccherotti et al. ..... | 623/13.11 |

FOREIGN PATENT DOCUMENTS

| | | |
|---|---|---|
| GB | 2 288 739 | 11/1995 |
| GB | 2 312 376 | 10/1997 |
| GB | 2 323 287 | 9/1998 |
| GB | 2 324 964 | 11/1998 |
| GB | 2 337 463 | 11/1999 |
| WO | WO 92/02196 | 2/1992 |

* cited by examiner

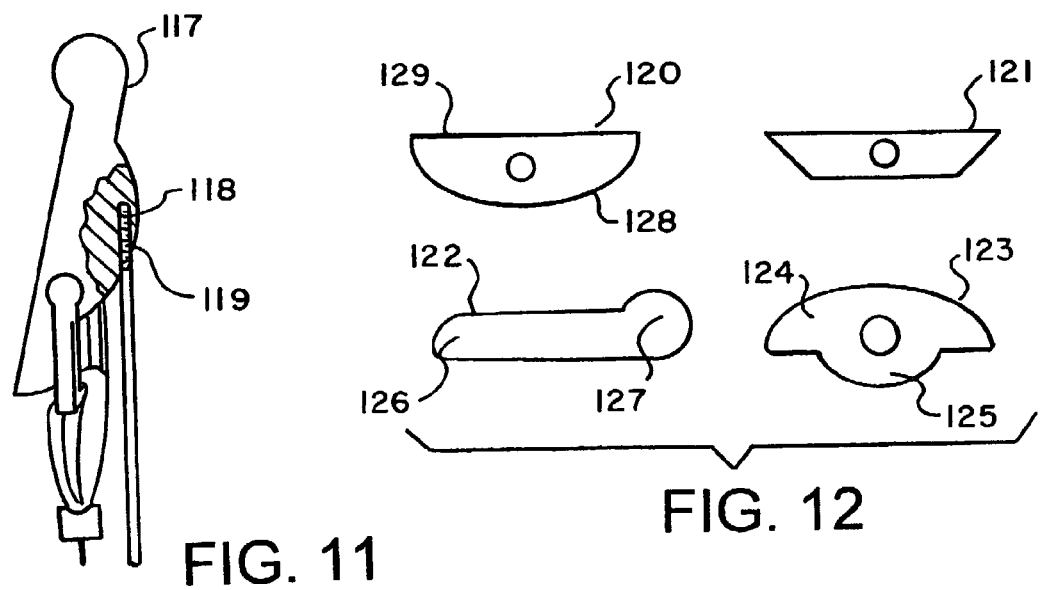
FIG. 11
FIG. 12
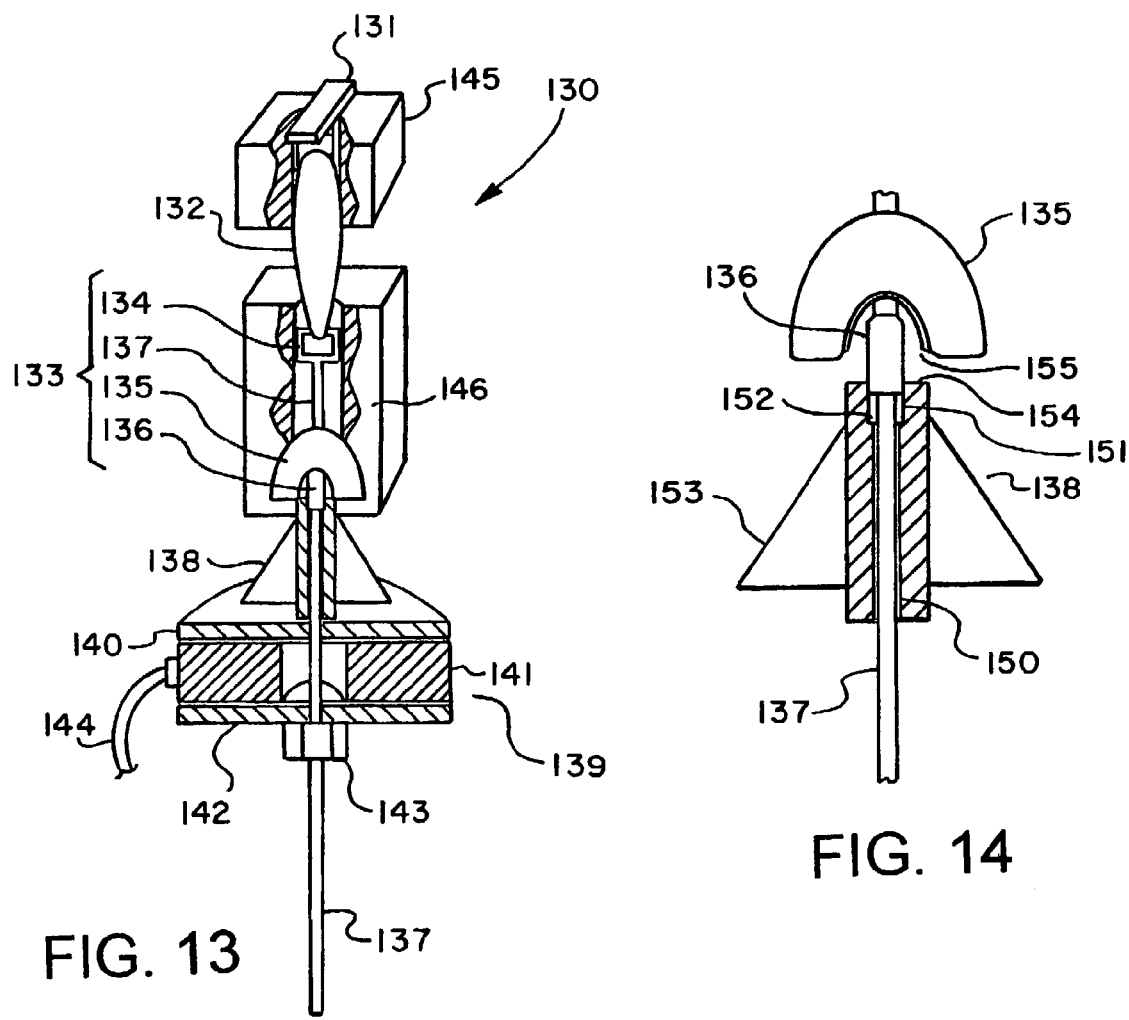
FIG. 13
FIG. 14

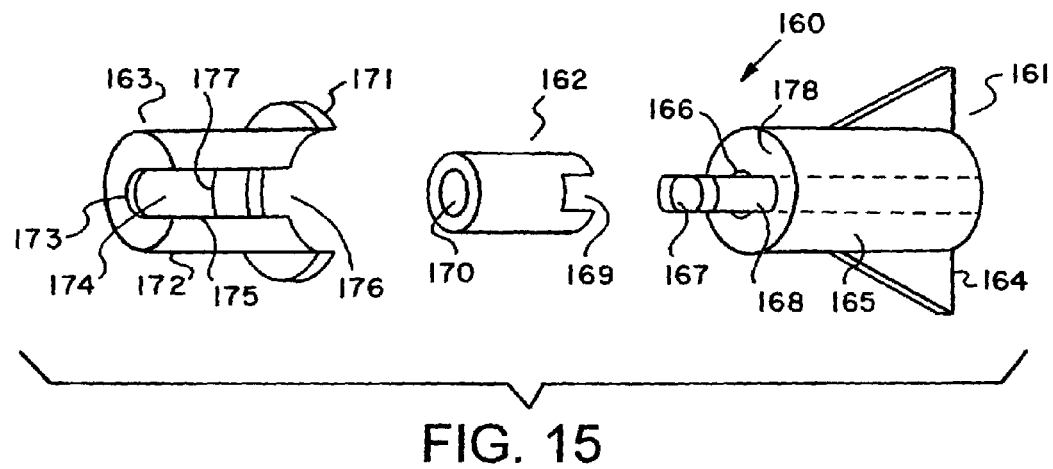
FIG. 15
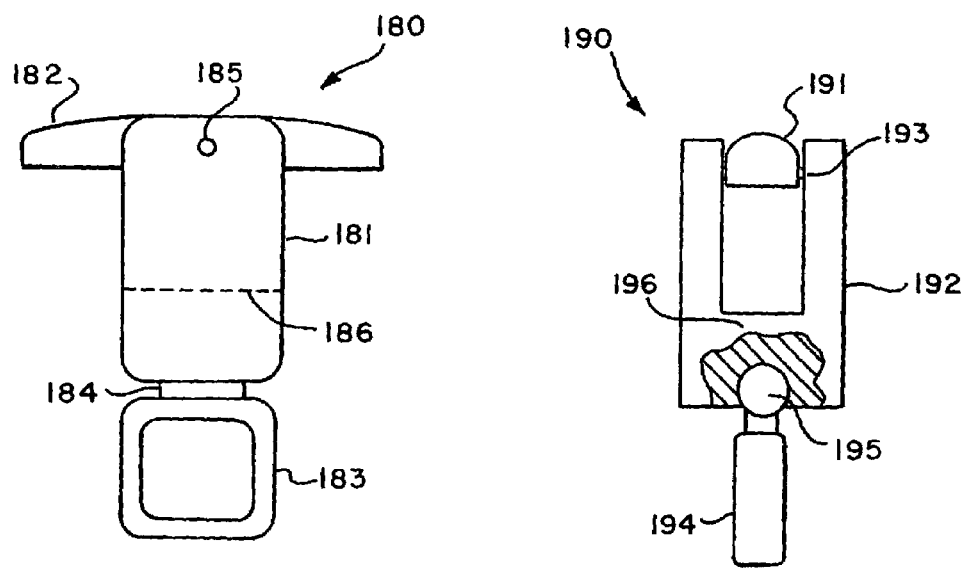
FIG. 16
FIG. 17

FLIP-WING TISSUE RETAINER

RELATED APPLICATIONS

This application is a U.S. national filing of PCT Application No. PCT/US00/27526, filed Oct. 7, 2000. The present application is also related to and claims the benefit under 35 U.S.C. §119(e) of U.S. Provisional Application No. 60/174,386, filed on Jan. 3, 2000 and U.S. Provisional Application No. 60/193,000, filed on Mar. 28, 2000.

FIELD OF THE INVENTION

The present invention concerns orthopedic medical devices, in particular, implantable orthopedic devices used to apply tension to biological tissues in a rapid manner or to facilitate orthopedic surgery. The present invention includes a flip-wing tissue retainer, a method of installing the tissue retainer, and a ligament tension-adjusting system incorporating the tissue retainer.

BACKGROUND OF THE INVENTION

The anterior cruciate ligament (ACL) spans the knee joint and attaches to the upper bone, the femur, and the lower bone, the tibia, to maintain smooth movement between their adjacent surfaces as the knee is bent. The ACL is known to tear during sporting accidents, thereby requiring replacement with a graft.

Orthopedic surgeons who conduct ACL repair, which includes replacement surgery, are continuously in search of methods and devices to improve the outcome of the surgery. A common problem in conventional ACL repair surgery is the lack of adjustability of the tension placed upon ligament graft, which results in poor graft performance. It is desirable, during installation of the ACL graft to keep the graft from becoming unduly twisted, since twisting of the graft causes it to become unduly stressed and thereby more prone to failure.

Conventional surgical techniques for repairing the ACL require drilling a bore through the tibia, across the knee jont and into the upper bone, the femur, and passing a ligament or tendon graft up the bore and fastening one end of the graft to the upper bone, the femur, and, attaching the opposite end of the graft to the Tibia. Typically, bone screws and bone staples are placed through the end of the ligament graft that protrudes from the bore, fastening it to the Tibia. Such fasteners are almost never removed and replaced during surgery to adjust ligament tension. Hence, if, during surgery, the replacement ligament in perceived to be loose, allowing excessive play between the upper bone, the femur, and the lower bone, the tibia, it is often left this way, leading to discomfort and pain in the knee postoperatively.

In methods where the ligament graft is attached to a femoral screw prior to surgery, with the attachment being where the ligament graft passes through a ring at the end of the screw, the screw is rotated into the femur and the ligament graft can twist and weaken during insertion.

When a pre-formed ligament or tendon is affixed to the femur with with prior art devices, the tissue is generally affixed to the surface of a bone with a screw with a ring at the end, a button with a loop of material to which the graft is attached, or other attachment means. Commercial embodiments of such devices that allow the graft to be preformed and attached to a ringed screw that screws into the femur, include the ACL Anchor System, manufactured by T.A.G. Medical Products of Israel. Embodiments of buttons and wing-like pieces that rest on the upper surface of the femur and are attached to a graft that is suppended below by a ring or loop, include, the ENDO-BUTTON™ by Smith and Nephew Endoscopy of Andover Mass., and the COBRA LFD™ by Atlantech Medical Devices of Harrogate, England.

In this last category of fastener, the button or wing-like device is rotated from the vertical position when it is being passed through the bore, to the horizontal position so that it sits on the surface of the femur, by marionette-like strings that are manipulated from above the femoral surface. The manipulation of these marionette-like strings requires that the strings are passed through the femoral bore and up through the muscle and skin above the femoral surface prior to installation of the device and then used to pull the device up through the bore and rotate it into position. This necessitates considerable finesse and requires additional incisions in the skin for the exit of the strings. For example, an incision would be required in the thigh and upper shin of a leg in order to install prior art devices. As the wing or button is not rotated via a solid shaft, but via strings, the surgeon cannot easily judge the exact position of the button or wing vis-à-vis the bone. With such devices, the button or wing, rather than resting on the bone, rests on soft tissue above the bone. As the button or wing works its way through the soft tissue, the graft becomes loose. Additionally, the tissue below the wing or button can necrose, resulting in less than optimal muscle function.

None of these devices include a flip-wing tissue retainer with an installation method as described herein. A need remains for a surgical method and device that overcomes the disadvantages inherent in conventional surgical methods of tissue repair.

SUMMARY OF THE INVENTION

The present invention overcomes at least some of the disadvantages of known related devices and thus is generally directed to orthopedic devices that can be used to control the amount of tension on a biological tissue or to facilitate orthopedic surgical procedures. The present invention provides a flip-wing tissue retainer, a system including the flip-wing tissue retainer, and a method of installation thereof. The flip-wing tissue retainer is easy to install, can be installed from a single opening in the tissue surrounding the bone and minimizes twisting of an attached ligament graft. Together with a tension-adjusting device, the flip-wing tissue retainer permits precise adjustment of the tension of the ligament graft.

In one aspect, the present invention provides a surgical method for repairing the ligament in a joint. The method includes the steps of:

forming an incision through tissue adjacent the joint to access a first surface of the upper portion of the inferior bone forming the joint;

forming a first bore that extends along a first direction from the first surface of the inferior bone through the joint surface of the inferior bone toward the superior bone;

forming a second bore that extends along a second direction from the joint surface of the superior bone to a second surface of the lower portion of the superior bone;

inserting a flip-wing tissue retainer, having a ligament graft engaged therewith, through the first bore and the second bore and beyond the end of the second bore by way of a tool; wherein the ligament graft optionally has engaged therewith a ligament-tensioning device; and if not already engaged, engaging a ligament-tensioning device with the ligament graft and installing and operating the ligament-tensioning device to adjust the tension of the ligament graft.

Specific embodiments of the invention include those wherein: 1) the ligament-tensioning device is a nut-type fastener having an eyelet engaged with the ligament graft; 2) the joint being operated upon is flexed prior to boring the second hole into the superior bone; 3) the first bore and second bore extend along approximately the same direction when the joint is flexed; 4) the above-described steps are performed with the superior and inferior bones interchanged such that the first bore is in the superior bone and the second bore is in the inferior bone; 5) incisions are closed after complete installation of the device; and/or 6) the flip-wing tissue retainer is initially installed by way of a guide-wire system.

Another aspect of the invention provides an orthopedic flip-wing tissue retainer comprising:

tissue-retaining means;

a flip-wing moveably engaged with the tissue-retaining means and comprising installation-tool engaging means; and a joint having a first half formed on the tissue retaining means and a second-half formed on the flip-wing.

Specific embodiments of the flip-wing tissue retainer include those wherein: 1) the installation-tool engaging means is a female receptacle; 2) the installation-tool engaging means is a smooth surface cavity, a threaded cavity, and/or a tapered cavity; 3) the flip-wing further comprises a deployment-tool engaging means for receiving a tool that deploys the flip-wing from an approximately vertical position to an approximately horizontal position during installation of the tissue retainer; 4) the deployment-tool engaging means is a receptacle; 5) the deployment-tool engaging means is adapted to engage a deployment-strap; 6) the deployment-strap is a wire, suture, string, cable, strap, rope or other similar device; 7) the tissue-retaining means comprises a hook, loop, eyelet, slot, clip, post, perforated plate, bar, ring, arcuate rod or geometrically-shaped hole; 8) the flip-wing has beveled edges; 9) the joint is a pivot joint, a pin joint, a universal joint, one whole or partial ball-and-socket joint, two opposing whole or partial bail-and-socket joints, a rotating joint or a hinge; and/or 10) the tissue-retaining means comprises a support engaged with the flip-wing and a hook, loop, eyelet, slot, clip, post, perforated plate, bar, ring, arcuate rod or geometrically-shaped hole.

Another aspect of the invention provides a tissue retainer comprising:

tissue-retaining means;

installation tool engaging means attached to the tissue retaining means;

deployment tool passageway attached to the tissue retaining means;

a flip-wing moveably engaged with the tissue-retaining means and comprising deployment-tool engaging means; and a joint having a first half attached to the tissue retaining means and a second-half formed on the flip-wing.

Specific embodiments of the tissue retainer include those wherein: 1) the installation-tool engaging means is a surface or a female receptacle, the deployment tool engaging means is a female receptacle, and the deployment tool passageway is a channel, bore, or tunnel; 2) the tissue-retaining means comprises a hook, loop, eyelet, slot, clip, post, perforated plate, bar, ring, arcuate rod or geometrically-shaped hole; 3) the joint is a pivot joint, a pin joint, a universal joint, one whole or partial ball-and-socket joint, two opposing whole or partial ball-and-socket joints, a rotating joint or a hinge; 4) the tissue-retaining means comprises a support engaged with the flip-wing and a hook, loop, eyelet, slot, clip, post, perforated plate, bar, ring, arcuate rod or geometrically-shaped hole; 5) the flip wing has a profile shape selected from the group consisting of a flat upper surface and an opposing convex surface; a trapezoid; a knobbed-end, a beveled end, and a lower convex surface; a larger convex upper surface and an opposing smaller convex surface; approximately the profile of a bird with a knobbed first end, convex curved underside and extended beveled second end; a beveled first end, a beveled second end, a lower convex surface and an upper convex or flat surface; a flat upper surface and a flat lower surface; an irregular upper surface and a flat or convex lower surface; and an arcuate upper surface and a flat or arcuate lower surface.

Another aspect of the invention provides a system for repairing or reconstructing a ligament in a human or animal joint. One embodiment of this aspect provides a system for replacing the torn ACL of a knee comprising:

a flip-wing tissue retainer for installation in a first bone of the knee;

a tension-adjusting device (otherwise referred to as a ligament-tensioning device) for installation in a second bone of the knee; and a ligament graft engaged with the flip-wing tissue retainer and the tension-adjusting device.

Some embodiments of the system, such as the FAS-TEN-ON™ system manufactured by T.A.G. Medical Devices of Kibbutz Gaaton, Israel, include those wherein: 1) the flip-wing tissue retainer is as described herein; 2) the tension-adjusting device comprises a threaded shaft; a nut threaded onto the threaded shaft; second tissue-retaining means disposed at one end of the threaded shaft; and a washer interposed the nut and the second tissue-retaining means; 3) the nut and washer together form a ball and socket joint; 4) the ball and socket joint is a flanged ball-and-socket nut assembly comprising an approximately hemispherical convex nut having an internal threaded bore for receiving a threaded shaft; an approximately hemispherical concave socket adapted to receive, mate with and retain the nut, the socket having a first hole or first notch through a portion thereof for receiving a portion of a threaded shaft engaged with the nut, wherein the hole or notch is smaller in size than the nut; and a flange attached to a portion of the periphery of the socket, the flange having a second hole or second notch through a portion thereof, wherein the second hole or second notch is sufficiently large in size to permit passage of the nut into the socket; 5) the nut further comprises second tool-engaging means adapted to receive a tool that can be used to drive or rotate the nut when engaged with a threaded shaft; 6) the second tool-engaging means comprises at least one recess; and 7) the inner surface of the washer has a ridge adapted to engage the tool used to drive the nut such that when the tension adjusting device is assembled, the second tool will be able to rotate and longitudinally displace the nut without abutting against a non-longitudinal surface of the nut, and thereby allowing tension adjustment of the ligament graft while being apprised of the tension within the ligament.

Other features, advantages and embodiments of the invention will be apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

FIG. 6b is a partial sectional side elevation of the tissue retainer of FIG. 6a.

FIG. 7a is side elevation of the tissue retainer of FIG. 6a.

FIG. 10b is a partial sectional front elevation of the flip-wing tissue retainer of FIG. 10a.

FIG. 11 is a partial sectional side perspective of a ninth embodiment of the flip-wing tissue retainer-based system.

FIG. 12 is a side elevation of alternate embodiments of the flip-wing.

FIG. 13 is partial sectional front perspective view of a second system according to the invention.

FIG. 14 is an inset of a portion of the system of FIG. 13.

FIG. 15 is an exploded view of an alternate ball-and-socket assembly and driving tool that can be used in the system depicted in FIG. 13.

FIG. 16 is a side elevation of a tenth embodiment of the tissue retainer.

FIG. 17 is a partial sectional front elevation of the ball an eleventh embodiment of the tissue retainer.

DETAILED DESCRIPTION OF THE INVENTION

The flip-wing tissue retainer of the invention can be used in various different types of ligament or tendon replacement or repair surgical procedures. Depending upon the ultimate surgical procedure being performed, a particular embodiment of the flip-wing tissue retainer will be preferred. The flip-wing tissue retainer and its method of installation are useful for reparation of injured knees, elbows, shoulders, ankles, wrists or hips and the ligaments and tendons associated with them in humans and animals. In the exemplary embodiments described herein, the flip-wing tissue retainer and an associated ligament graft are used to replace the ACL in a human knee.

Figure 1:
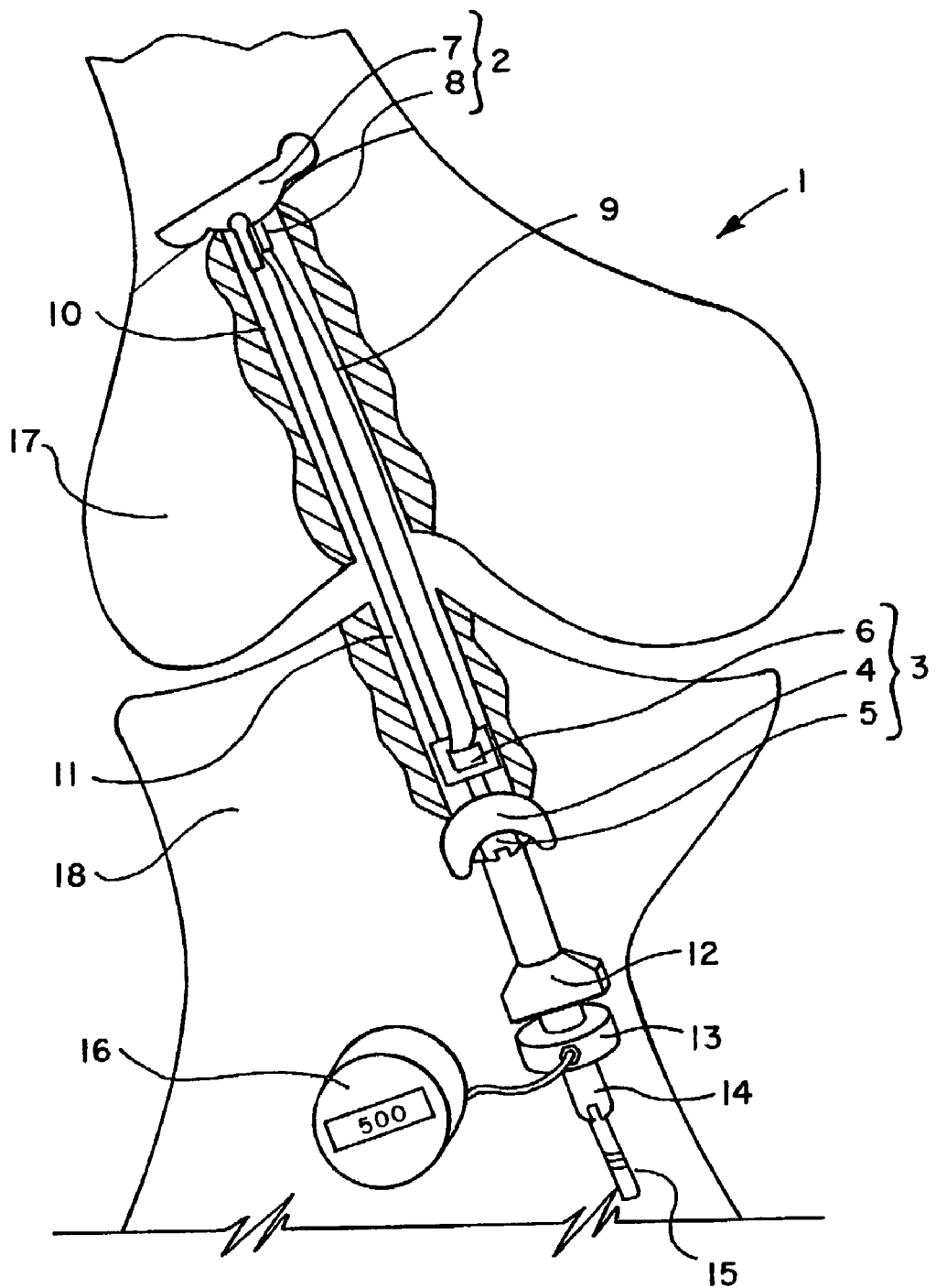
FIG. 1 is a side elevation with a partial sectional view of a human knee joint having a flip-wing tissue retainer and associated tissue-tensioning device installed therein.
Figure 2A:
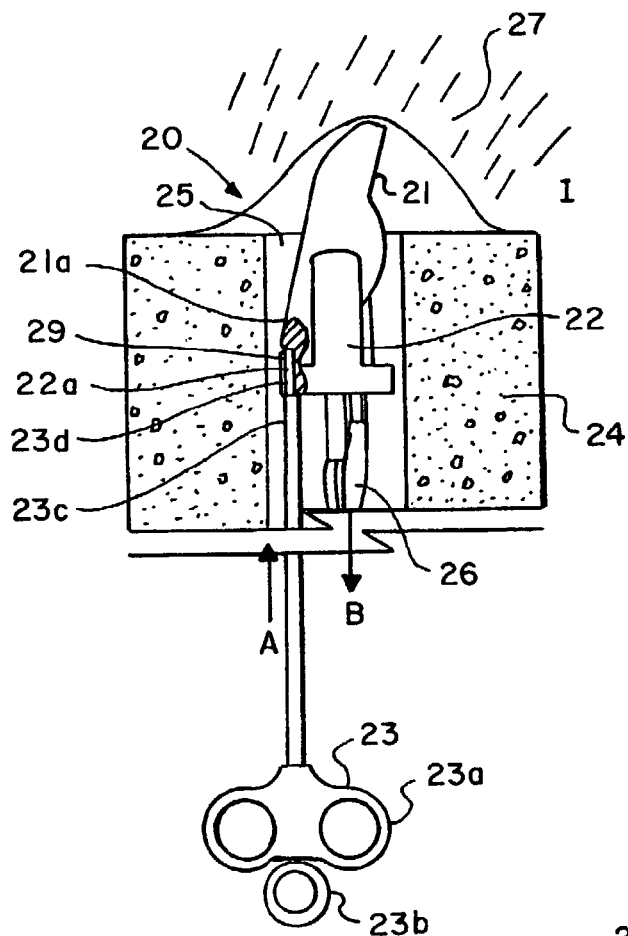
FIGS. 2a–2d are partial sectional side elevations of a first embodiment of the tissue retainer being installed and deployed.
Figure 2B:
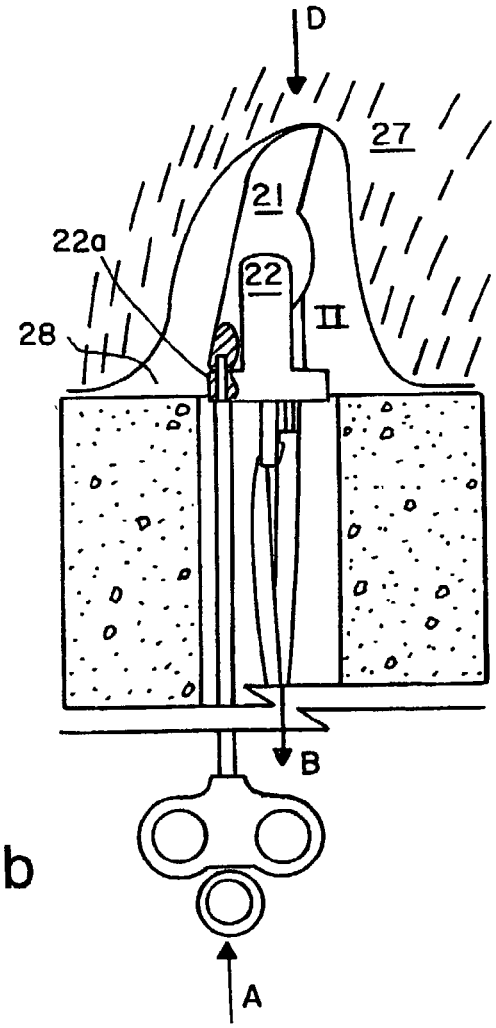
Figure 2C:
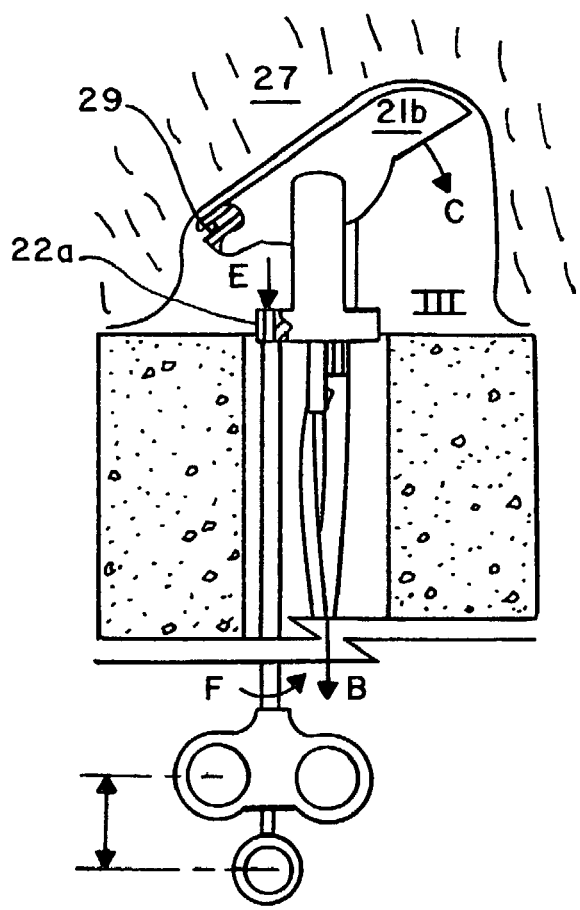
Figure 2D:
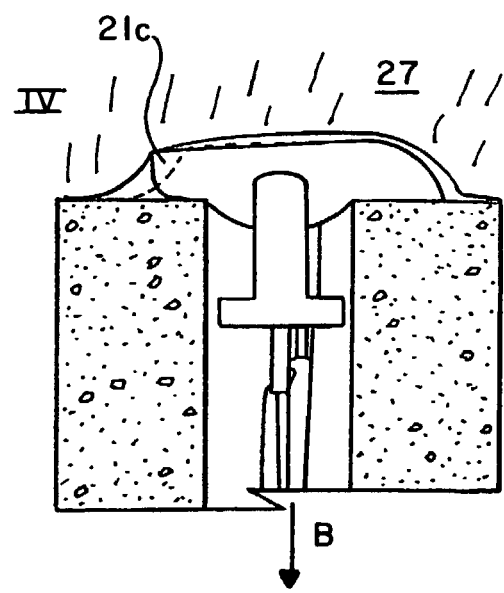

FIG. 1 depicts a ligament replacement system (1) installed in the knee of a human. The system comprises a flip-wing tissue retainer (2) installed in a bore (10) in the femur (17). The flip-wing tissue retainer comprises a flip wing (7) and tissue-retaining means (8). The tissue retainer is engaged with a first end of a ligament graft (9). The second end of the ligament graft is engaged to a tension-adjusting device (3). The tension-adjusting device comprises a second tissue-retaining means (6), a washer (4), a threaded nut (5), and a threaded shaft (15). The tension-adjusting device is installed in a bore (11) in the tibia (18). Together the tissue retainer (2), ligament graft and tension-adjusting device provide a ligament replacement system.

One method of installing the system of FIG. 1 proceeds as follows. A bore (10) is drilled from an outer vertical surface of the upper portion of the tibia (18) through the knee-joint surface of the tibia. This bore (10) is then continued and drilled through the knee-joint surface of the femur (17) to an outer vertical surface of the lower portion of the femur. The bores are generally sized such that the flip-wing tissue retainer (2) can be passed through them. The bores (11) and (10) are drilled with the knee flexed so that they extend along a common linear axis when the femur and tibia are at a predetermined position with respect to one another, such as when the knee is flexed.

Referring now to FIGS. 2a–2d, the tissue retainer (20) is then passed through the bore in the tibia (not shown) and the bore (25) in the femur (24) by way of the tool (23) that is engaged with the flip-wing (21), by way of the receptacle (29), and the tissue retaining means (22), by way of the deployment tool passageway (22a). The tool (23) is a combination installation/deployment tool, since it is used to both install the tissue retainer (20) and deploy the flip-wing (21). Upon exiting the bore (25), the flip-wing contacts an overlying muscle mass (27). The tissue retainer is pushed in the direction of the arrow (A) with the tool (23) by way of its shaft (23c) that abuts a surface of the tissue retaining means (22). Generally, the handles (23a, 23b) are pushed in the direction of the arrow (A) in order to install the tissue retainer. During installation, the muscle mass (27) is stretched from the femur thereby forming the first position (I). The ligament graft (26) is already engaged with the tissue retaining means (22) prior to placing the tissue retainer in the bore (25). Once the bottom end (21a) of the flip-wing is above the surface (28) of the femur, the pin (23d) is pulled out of the receptacle (29) by pulling the handle (23b) in the direction of the arrow (B). The muscle mass forces the top end (21b) of the flip-wing downward in the direction of the arrow (C). The tool (23) is pulled in the direction of the arrow (B) by way of the handle (23a) and the graft is pulled in the direction of the arrow (B) so that the end (21a) contacts the bone surface (28). The muscle mass and the downward pull on the graft in direction (B) forces the flip-wing to lie along the surface of the bone (28). Once the flip-wing is in the position III, the tool is then disengaged from the tissue-retaining means (22) by pulling the tool in the direction of the arrow (E), and optionally turning in the direction of the arrow (F), for example, if threaded engagement is used. In the device of FIGS. 2a–2d, the tool uses the outer tube (23c) to brace against the installation tool engaging means of the tissue retainer (22) to remove the pin from the wing (21). The tissue retaining means depicted in these figures includes, e.g. has attached thereto, a deployment tool passageway (22a) and an installation tool engaging means; while the flip wing includes a deployment tool engaging means (29).

The flip-wing (21) includes a flat upper surface, a convex lower surface, a first downwardly beveled end and a second upwardly beveled end. The flip-wing can also have two downwardly beveled ends (21b) and (21c in phantom).

Figure 3A:
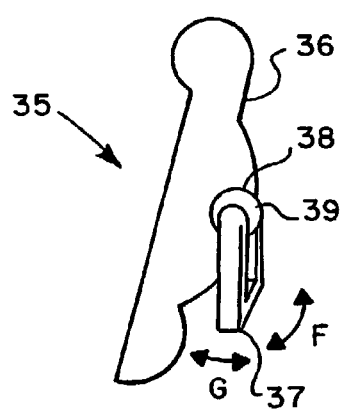
FIGS. 3a and 3b are perspective side views of a second embodiment of the tissue retainer.
Figure 3B:
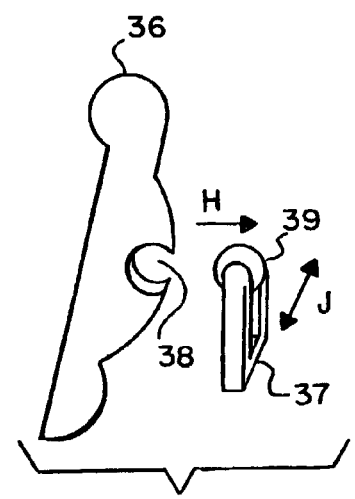
Figure 4A:
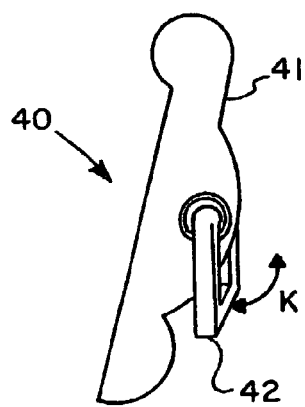
FIGS. 4a and 4b are perspective side views of a third embodiment of the tissue retainer.
Figure 4B:
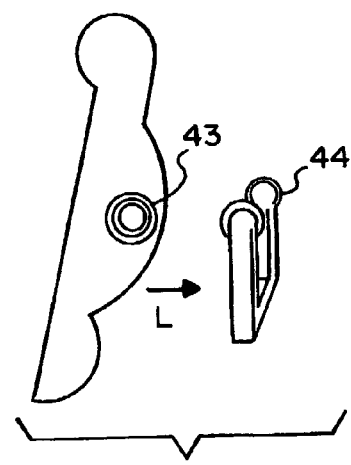
Figure 5A:
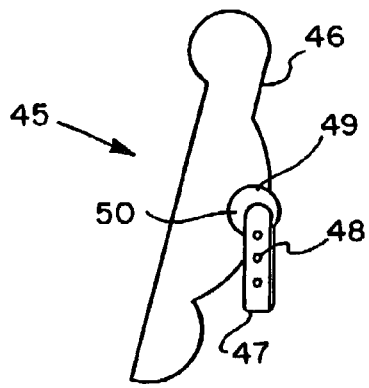
FIGS. 5a and 5b are perspective side views of fourth and fifth embodiments of the tissue retainer.
Figure 5B:
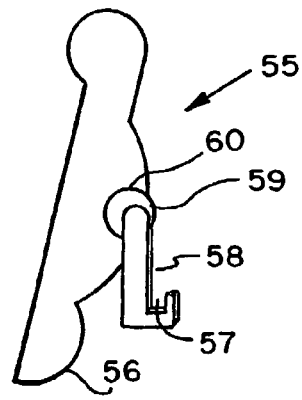

Many different embodiments of the tissue-retainer can be used. The tissue retainer (35) depicted in FIGS. 3a–3b comprises a flip-wing (36) engaged with tissue-retaining means (37) by way of a ball (39) and socket (38) joint. This type of joints allows the tissue-retaining means to pivot forward and backward (arrow G) and side-to-side (arrow F) as well. The tissue retainer (40) depicted in FIGS. 4a–4b comprises a flip-wing (41) engaged with tissue-retaining means (42) by way of two opposing ball and socket joints (43, 44). The ball and socket joints can independently comprise partial or complete balls and sockets. This type of joint allows the tissue-retaining means to pivot forward and backward (arrow K). The tissue-retaining means (42) can be snappingly engaged with the flip-wing. The tissue retainer (45) depicted in FIG. 5a comprises a flip-wing (46) engaged with tissue-retaining means (47) by way of a hinge or pin joint (49, 50). The tissue-retaining means comprises one or more holes or apertures (48) for engaging the tissue. FIG. 5b depicts the tissue retainer (55) comprising a universal joint (59, 60), a flip-wing (56) and hook-shaped tissue-retaining means (58). The hook comprises a receiving area (57) for engaging with a loop of ligament tissue. This type of joints allows the tissue-retaining means to move in any direction, including rotation with respect to the flip-wing.

Figure 6A:
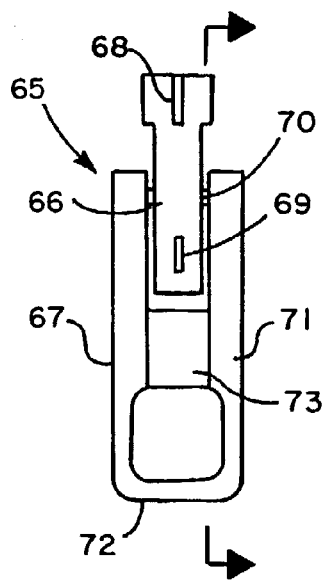
FIG. 6a is a front elevation of a sixth embodiment of the tissue retainer.
Figure 6B:
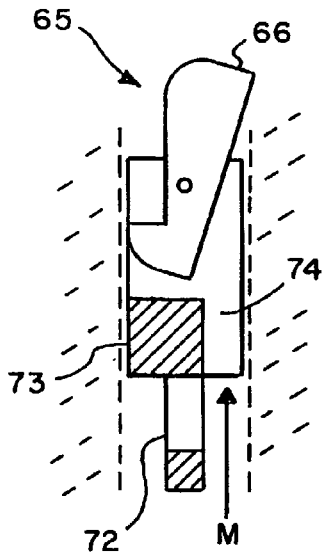

FIGS. 6a and 6b depict the tissue retainer (65) that comprises a flip-wing (66) and tissue-retaining means (67) comprising two support members (71), tissue-engaging means (72) and an optional transverse support (73) connecting the support members. The tissue-retaining means is engaged with the flip-wing by way of a pivoting pin joint (70). The flip-wing comprises installation-tool engaging means (68) and deployment-tool engaging means (69). The tissue retainer comprises an installation-tool passageway (74), which can be a notch, channel, groove or bore in the tissue-retaining means. When installed in a bone (shown in phantom), the inner surface of the bore in the bone and a portion of the tissue-retaining means define the passageway (74). The passageway can also be used as a passageway for a deployment-tool.

Figure 7A:
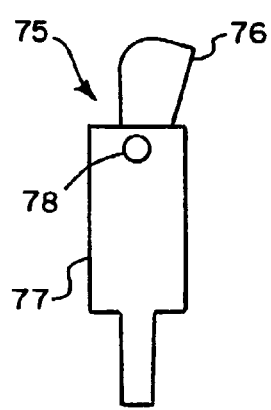
Figure 7B:
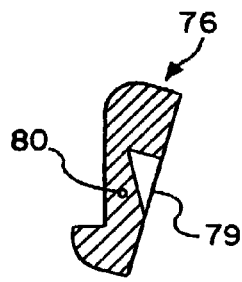
FIG. 7b is a sectional side elevation of the flip-wing of FIG. 8.

Referring now to FIGS. 7a and 7b, the tissue retainer (75) comprises a flip-wing (76) engaged with tissue-retaining means (77) by way of a pin joint (78). The flip-wing comprises a receptacle (79) that functions as an installation-tool engaging means. The hole (80) receives the pin of the pin joint.

Figure 8:
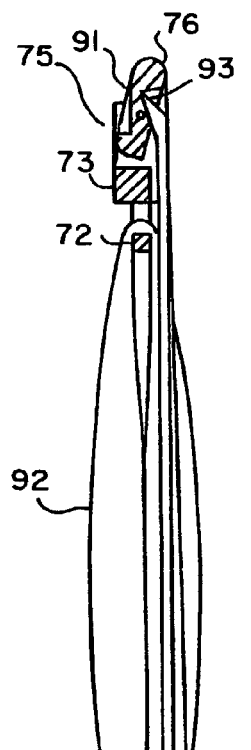
FIG. 8 is a partial sectional side elevation of an alternate embodiment of the system of the invention.

FIG. 8 depicts a system comprising the tissue retainer (75), the ligament graft (92), the threaded shaft (87) and tissue-retaining means (86) of a tissue-tensioning device, the installation-tool (88), and the deployment-tool (91). The installation-tool (88) has a male tip (93) that engages the installation-tool engaging means (79). The deployment-tool (91) is a strap, suture, cord, string, rope, wire, cable or other similar element. The deployment tool is engaged with the handle (89) of the installation-tool by way of the retainer (90). The distal end of the deployment-tool engages the deployment-tool engaging means (69) of the flip-wing, superposes the flip-wing, and runs along side the installation-tool. This tissue retainer is installed by pushing the flip-wing in its vertical position with the installation-tool until the flip-wing is above the surface of the femur and then pulling the deployment-tool to deploy the flip-wing into its horizontal position. Finally, the installation tool is pulled and disengaged from the flip-wing.

Figure 9:
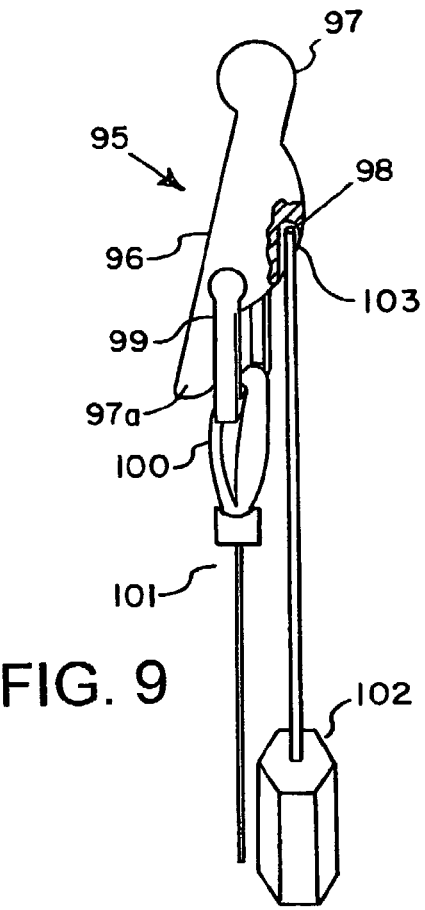
FIG. 9 is a partial sectional side perspective of a seventh embodiment of the flip-wing tissue retainer-based system.
Figure 10A:
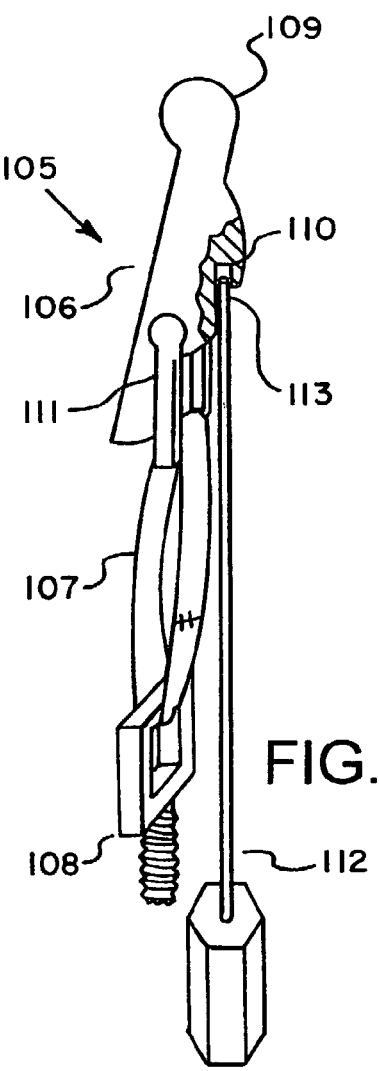
FIG. 10a is a partial sectional side perspective of an eighth embodiment of the flip-wing tissue retainer-based system.
Figure 10B:
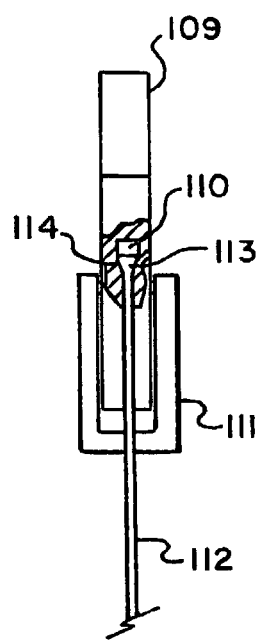

FIGS. 9–11 depict additional embodiments of the ligament replacement system (95, 105) employing a tissue retainer. The tissue retainer (96) comprises a smooth surfaced cavity (98) adapted to receive the tip (103) of the installation-tool (102). In this embodiment, the installation-tool simply slides out of the receptacle (98) and cannot be used to pull the flip-wing as the end (97a) of the flip wing (97) engages the bone surface. The tool (102) generally cannot be removed from the tissue retainer (96) until the end (97a) rests on the bone surface. The tissue retainer (106) comprises a tool engaging means (110) which is a tapered cavity adapted to receive and engage the male end (113) of the installation tool (112). The female receptacle (110) will receive the tip (113) when the tool (112) is pushed upward during installation of the tissue retainer. When ready, the tool (112) is pulled thereby pulling the flip-wing (109) down and deploying the flip-wing. This type of operation is possible since the receptacle (110) has a tapered surface (114) that permits temporary retention of the receptacle with the tip (113) even when the tool (112) is pulled. In a like manner, the tip (113) has a tapered surface that is generally adapted to mate with the tapered surface of the receptacle (110). The tissue retainer (117) comprises a threaded installation-tool engaging means (118) adapted to mate with the threaded end (119) of an installation tool. In this and other embodiments, the installation tool can also serve as the deployment tool.

FIG. 12 depicts the side elevation view of various different embodiments of the flip-wing. The flip-wing (120) comprises a flat surface and an opposing curved surface. The flip-wing (121) has an essentially trapezoidal profile. The flip-wing (122) comprises a knobbed-end (127) and a beveled end (126). The flip-wing (123) comprises a larger curved surface (124) and an opposing smaller curved surface (125). In FIG. 11, the flip-wing (117) has a profile that approximates that of a bird with a knobbed first end, convex curved underside and extended beveled second end. In each embodiment, the flip-wing is narrower than the diameter of the bore into which it is installed.

FIG. 13 depicts one embodiment of the tension gauge used to measure the amount of tension on a ligament graft being installed. The tissue replacement system (130) comprises the tissue retainer (131) engaged with the ligament graft (132) which is engaged with the adjustable tension-adjusting device (133). The device (133) comprises a threaded shaft (137) having an integral tissue-retaining means (134) engaged with the ligament graft. The device also comprises a socket-shaped washer (135) and a curved-surface nut (136) engaged with the threaded shaft. By threading the nut about the threaded shaft, the tension upon the ligament graft is adjusted.

The tension on the ligament graft is easily measured using the system depicted in FIGS. 13–14. The entire system (130) is assembled and the nut (136) is tightened about the threaded shaft with the key (138) until slight tension is placed upon the ligament graft. The tension gauge (139) and compression nut (143) are installed onto the threaded shaft (137). The key (138) has a longitudinal bore (150) that is larger in diameter than the threaded shaft such that the key can be moved up and down the shaft without being threaded. The key has an end (154) that engages with a shoulder (155) on the inner surface of the socket (135). The key also comprises grasping portions (153) to permit turning by hand. The assembly of the key, nut and washer is designed such that the end (154) can glide on the shoulder (155) while rotating the nut (136). In addition, the nut will be able to move longitudinally up and down the threaded shaft a distance without displacing the key longitudinally relative to the threaded shaft. Using this configuration, the compression nut (143) is tightened down onto the tension gauge (139) until the desired tension is displayed on an attached display (not shown). The tension gauge comprises opposing washers (140, 142) and an interposed pressure transducer (compression measuring device) (141). By tightening the compression nut (143), tension is placed upon the ligament graft while simultaneously displacing the washer (135) from the nut (136). This is possible, since the end (154) of the key can contact the shoulder (155) of the washer without the nut (136) contacting the inner surface of the washer. Once the desired tension is achieved, the nut (136) is tightened down with the key onto the inner surface of the washer until the gauge display reads "0", i.e., the nut (136) has assumed the load previously carried by the compression nut (143). The load can be initially set at a lower value and zeroed out. The ligament is generally allowed to set in a first position under tension so as to stretch it out. The load on the force cell is then set to a slightly higher value and then the nut (136) is turned with the tool (138) until it is zero load is achieved by the compression nut. The above step(s) can be repeated a number of times until the ligament is fully stretched as indicated by the force gauge (142) after each adjustment.

An alternate embodiment of the key, washer and nut assembly (160) is depicted in FIG. 15. The key (161) comprises a tubular body (165) having a bore (166) with a diameter larger than that of a threaded shaft it can receive. The key also comprises grasping means (164), an abutment end (178) and slot-engaging means (167, 168). The nut (162) comprises a threaded bore and a slot (169) adapted to engage with the slot-engaging means (167, 168). The nut is generally a ball-shaped, hemispherical or curved-surface nut that is adapted to cooperate with the washer (163) to form a whole or partial ball-and-socket joint. The washer (163) comprises a flange (171), a socket (176, 174) and a longitudinal slot (175) cut through the socket. The washer also has a shoulder (177) within the socket to receive and engage the abutment end (178) of the key. The deeper portion (174) of the slot is adapted to receive the body of the nut. The dimensions of the individual components of this assembly (160) are designed such that when the three are assembled and the abutment end engages the shoulder (177), the key will be able to rotate the nut without having to rotate the washer. In other words, the nut will be able to move longitudinally within the socket even when the abutment end engages the shoulder.

FIGS. 16 and 17 depict additional alternate embodiments of the tissue retainer (180, 190). The tissue retainer (180) comprises a flip-wing (182) pivotally (180) engaged with tissue retaining means comprising two upright supports (181), a tissue engaging means (183), a threaded joint (184) formed between the tissue retaining means and the upright supports and an optional transverse support (186) connecting the upright supports (181). The tissue retainer (190) is of substantially the same construction as the tissue retainer (180) except that the joint (195) is a ball-and-socket joint.

Figure 18:
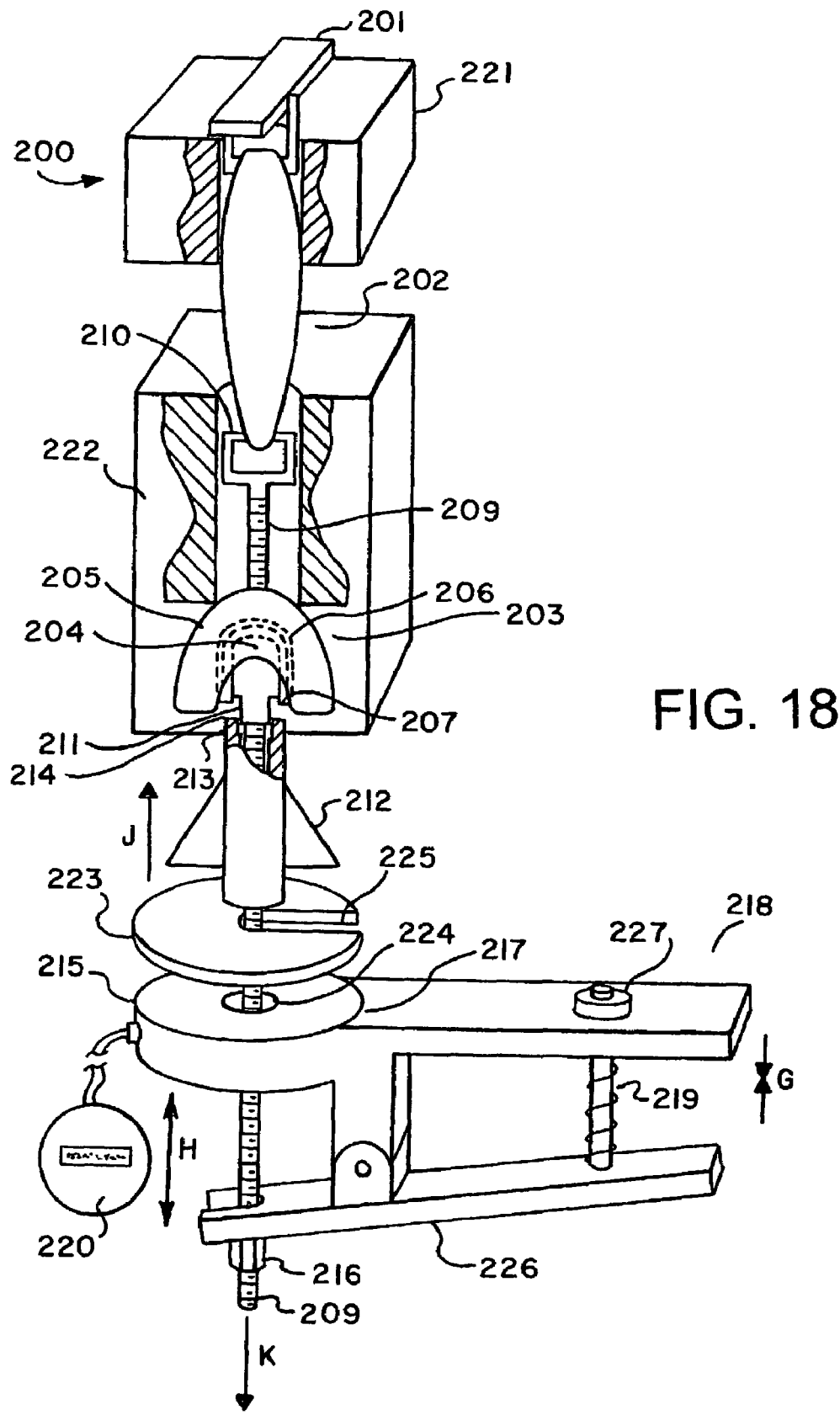
FIG. 18 is a partial sectional front perspective view of another alternate system according to the invention.

The system (200) depicted in FIG. 18 comprises a variety of previously described elements and other additional ones. The tissue retainer (201) is implanted in the femur (221) and engaged with the ligament graft (202). The tension-adjusting device (203) is installed in the tibia (222) and comprises a socket-shaped washer (205), a threaded shaft (209), tissue-retaining means (210) at the end of the threaded shaft, and nut (204) having a curved surface that can form a ball-and-socket joint with the washer. The inner surface of the washer comprises a shoulder (207) and a receptacle (206), which is adapted to receive the nut (211). The receptacle (206) has a large width to accommodate the nut (211) and allow the ball and socket arrangement to assume a variety of incident angles with respect to one another. This is advantageous as the bone (203) can have an irregular surface that causes the washer to lie at an oblique angle. The play between the nut and the washer allows the washer to sit at this angle without putting pressure on the shaft (209). The key (212) is used to rotate the nut (204) about the threaded shaft. The nut comprises one or more slots (211) adapted to engage one or more respective male engaging means (213) of the key. The key also comprises an abutment end (214) which is adapted to slidably engage the shoulder (207) when the male engaging means (213) engage the slot(s) (211). In this way, the nut (204) can be threaded down the shaft a distance by the key without changing the longitudinal positions of the washer and key relative to the threaded shaft.

In order to adjust the tension upon the ligament graft (202) to a specific value, the tension gauge (215), a corresponding compression nut (216) and a washer (223) are mounted onto the threaded shaft adjacent the end of the key distal to the washer (205). Typically, the nut (204) and the compression nut (216) are alternately tightened a number of times while adjusting the tension on the ligament graft until the desired tension is placed on the ligament graft. The number of times that the alternating tightening occurs can be minimized by employing a biasing tool (218) that comprises a biasing mechanism (219), such as a spring, and two opposing extended members (217, 226) that are hingedly engaged. The biasing tool (218) is used to maintain a relatively constant predetermined pressure between the washer (223), the key (212) and the socket-shaped washer (205) and thereby a constant tension on the ligament graft (202) by way of the threaded shaft (209). The tension gauge (215) is attached to one member (217) of the biasing tool and is placed adjacent the slotted (225) washer (223). The compression nut (216) is placed adjacent an opposing surface of the other member (226). By adjusting the force exerted on the members (217, 226) by the biasing means (219) and the adjuster (227) in the direction of the arrows (G), the opposing force between the opposite ends of the biasing tool (218) is adjusted in the direction of the arrows (H). In this manner, the biasing tool exerts a first force upon the compression nut (216), and thereby the threaded shaft (209), in the direction of the arrow (K) and a second opposing force on the washer (223), the key (212), the socket-shaped washer (205) and the tibia (222) in the direction of the arrow (J), thereby tensioning the ligament graft (202). The display (220) is operably engaged with the tension gauge to display the tension being placed upon the ligament. Once the desired tension is displayed, the key (212) is turned thereby threading the nut (204) further into the receptacle (206) until the nut assumes the load carried by the compression nut (216). Once the nut (204) engages the washer (205) with sufficient pressure, it will assume a force load about equal to the tension being applied on the ligament by the biasing tool. If the tension is to be increased, the compression nut (216) is threaded toward the tension gauge further and the above-steps repeated until the nut (204) assumes the load previously carried by the compression nut (216).

One advantageous feature of the tissue retainer of the invention, is that it can be installed without guide wires and without having to make a second incision in the tissue overlying the opposing surface of the second bone, i.e, only one incision through the tissue adjacent the first bone of a joint is required to install the tissue retainer. In addition, the embodiment depicted in FIGS. 2a–2d, permits unprecedented control of deployment of the flip-wing.

Since the tissue-retaining means can be rotatably engaged with their respective elements, twisting of the ligament graft is minimized, with respect to conventional devices such as the tissue anchor by T.A.G. Medical, or eliminated. The graft (202) can be fully sutured into a loop, integral to both the lower tissue retaining piece, (210) and the upper tissue retaining piece (201). This makes the procedure more precise as the graft can easily be formed to a specific length. Such a graft loop can also be easily fashioned into a very strong construct. The tissue engaging means can be thinner, thicker or of the same thickness as the rest of its respective elements.

If a second incision is made, a guide-wire can be used to pull the tissue retainer into its respective bore concomitantly with, or in place of, the installation-tool. The guide-wire can be a wire, string, strip, strand, thread, braided lace or other equivalent object that is small enough to pass through the bores in the bones and strong enough to aid in installing the tissue retainer. Artisans in the field sometimes refer to these devices as marionette strings. The guide-wire can be made of cotton, silk, suture, polymer, plastic, metal, cotton, wool, natural fiber, synthetic fiber, or a combination thereof. The guide-wire is generally 1/32" to 1/4" or 1/16" to 1/8" in diameter.

The end of the installation-tool can be shaped as a standard screw driver, Phillips screw-driver, Allen wrench, multi-sided shaft, square-ended screw driver, blunt end, pointed end, tapered end, star screw driver and other such male driving tools adapted to engage a female receptacle. As depicted in FIGS. 2a–2d, a combination installation/deployment tool can be used to install the tissue retainer.

The retainer optionally includes a suture that is used to engage a biological tissue with the tissue retainer, generally after the tissue retainer is in place. For example, the ligament graft, which comprises a loop of ligament tissue, can be fully formed and attached to the tissue retainer prior to insertion of the flip-wing tissue retainer to provide a strong connection between the soft tissue and the bone. Alternatively, the flip-wing tissue retainer is implanted in the bone first, and then the ligament tissue is engaged with the tissue retainer via the suture that passes through the tissue retainer.

The tissue-retaining means can be shaped as desired provided it operates to retain a ligament graft after installation of the flip-wing tissue retainer into a bore in a bone. The tissue retaining means can be shaped as a bar, hook, arcuate rod, ring, circle, oval, square, triangle or other geometric shape. The edges of the tissue retaining means can be beveled to minimize wear of an engaged ligament graft.

The flip-wing tissue retainer and its elements are made of durable materials that retain their physical integrity during use. The material of construction for each element of is independently selected from the group consisting of plastic, metal, alloy, rubber, silicone rubber, dissolvable or degradable plastics (such as poly(galactic acid)), and combinations thereof.

As described herein, the term "ligament graft" refers to fibrous tissue taken from another piece of living tissue, such as strands of muscle tissue, muscle covering or tissue substitute. The ligament is generally made from a biological tissue but can also be made of synthetic materials, such as gortex, or biologically compatible material, such as collagen. It can be made from an allograft, meaning tissue that was harvested from an other individual and properly sterilized, such as the preserved tendon of CryoLife™ Inc. The ligament graft is generally a portion of ligament or tendon that has been sutured. This fibrous tissue is generally formed into a continuous loop of tissue by passing it through the tissue retainer and suturing the two ends together. When engaged with the tissue retainer, the location in the graft where the two ends of the tissue meet is generally not directly adjacent the tissue retainer. The graft loop can be formed from two concentric bands, so that there are four strands of ligament suspended between the two tissue retainers. The graft can be formed from one or two tendons, such as the gracilus and semitendinosis. It is also possible that only one ligament is required to make the dual band, four-strand graft construction. This is because the two tissue retainers are long and within the bone tunnel so that the span that must be occupied by the graft is shortened.

To reinforce the ligament graft, the loop can be tensioned and the two strands that are adjacent and parallel are sutured side-by-side. The side-by-side suturing may be done before or after installation onto a tissue retainer; although, it is generally done afterwards.

When a second fastener such as the tissue-tensioning device described above is utilized, the tissue-retaining means of the second fastener is also generally attached directly to the tissue loop prior to attaching the two ends of tissue together and then suturing the tissue strands side-to-side. This provides a strong continuous loop of tissue that spans between the two tissue-retaining means.

For the purposes of the present invention, any suitable tension-adjusting device can be used in combination with the flip-wing tissue retainer. Exemplary tension-adjusting devices are depicted in FIGS. 1, 13 and 18. Additional tension-adjusting devices are disclosed in International Publication No. WO 92/02196 to J. D. Pauland United Kingdom Patent No. GB 2337463 A to J. S. Woods the entire disclosures of which are hereby incorporated by reference.

A conventional nut and flat-washer combination can be used with the tension-adjusting device. Alternatively, the nut and washer used with the tension-adjusting device can be a ball-and-socket nut assembly, for example as described herein. An internally threaded nut has a convex-shaped outer surface. A mating nut retainer has a washer or flange and a concave-shaped socket that is adapted to receive the convex-shaped surface of the nut. When the nut assembly is implanted into a bone, the flange will preferably be disposed on the surface of the bone, the socket will be disposed within a bore in the bone, and the nut will be disposed within the socket. The flange and socket will each have a bore or notch through which a threaded shaft engaged with the nut can pass. A nut assembly of this kind will permit implantation of bolts into bone at many different incident angles, i.e., one single ball-and-socket nut assembly can be used to implant many different types of bolts and many different incident angles relative to the surface of the bone.

At least a portion of the flange is disposed on the surface of the bone. With the ball-and-socket configuration, the threaded shaft of the tension-adjusting device can be disposed at different incident angles with respect to the surface of the bone and to the flanged cup. The actual incident angle of implantation will depend upon the incident angle at which the bore through the bone is made. This diverse use is due to the swiveling of the nut within the socket and to the notches and/or bores through the flange and socket. This construction allows the threaded shaft to rotate and swivel in a variety of angles within the flanged cup to fit a variety of brothels or bores in the bone. A bore in the bone can be countersunk.

Any threaded shaft can be used in the tissue-tensioning device. The threads on the threaded shaft can be any known threads used in orthopedic devices. Generally, machine, wood, fine metal or buttress threads can be used. Buttress threads generally have a long slope on one side and a short slope on the other.

The tissue retainer can be used to attach virtually any soft tissue to bone, or cartilage, and hold it against the bone until it heals and adheres to the bone, with greater precision of tension than traditional suture and anchor combinations. It also holds stronger than many screw-type tissue anchors such as the Phantom absorbable screw and the M. Kurosaka Advantage screw, both by DePuy OrthoTech. For example, muscle that has ripped free from its attachment to the bone can be reattached to the bone, or, for paralytics, muscle can be cut free from its mooring to a bone and transferred and attached to another location. In these cases, the fibrous end of the muscle, the tendon, is passed through the tissue retainer and sutured into a strong loop of tissue by way of a suture. After attachment of the tissue, the flip-wing tissue retainer is easily installed into the bone without twisting the attached tissue.

"Soft tissue", "biological tissue" or "tissue" as used herein generally refers to any tissue in the body that requires attachment to a bone, e.g., ligament that has avulsed from its bone.

Where the ligament has ripped in the middle, it is usually not possible to simply take the end of the ripped ligament and reattach it to the bone. In this case, as noted above, the fibrous portion of the muscle is harvested from the human or animal body and sutured into a continuous loop, reinforced via side-to-side sutures and then attached to the bone via the flip-wing tissue retainer.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

The invention claimed is:

1. A system for repairing or reconstructing a ligament in a human or animal joint, the system comprising: a flip-wing tissue retainer for installation in a first bone of the joint; a tension-adjusting device for installation in a second bone of the joint; and a ligament graft engaged with the flip-wing tissue retainer and the tension-adjusting device, the system further including a:

ball-and-socket nut assembly comprising a convex curved surface nut having an internal threaded bore for receiving the tension-adjusting device; a concave socket adapted to receive, mate with and retain the nut, the socket having a first hole or first notch through a portion thereof for receiving a portion of the tension-adjusting device engaged with the nut, wherein the hole or notch is smaller in size than the nut; and a flange attached to a portion of the periphery of the socket, the flange having a second hole or second notch through a portion thereof, wherein the second hole or second notch is sufficiently large in size to permit passage of the nut into the socket.

2. The system of claim 1, wherein the nut further comprises tool engaging means adapted to receive a tool that can be used to drive or rotate the nut when engaged with the tension-adjusting device.

3. The system of claim 2, wherein the tool-engaging means comprises at least one recess.

4. The system of claim 2, wherein the tension-adjusting device includes a washer interposed between the nut and a tissue-retaining means at one end of the tension-adjusting device, the washer having a shoulder adapted to engage the tool used to drive the nut such that when the tension-adjusting device is assembled, the tool will be able to rotate and longitudinally displace the nut without having to rotate or longitudinally displace the washer and thereby tension the ligament graft.

* * * * *